(12) United States Patent
Weisshaar et al.

(10) Patent No.: US 12,145,156 B2
(45) Date of Patent: Nov. 19, 2024

(54) CONFIGURABLE DEVICE ARRANGEMENT FOR PERFORMING AT LEAST ONE UNIT OPERATION IN A BIOPHARMACEUTICAL PROCESS

(71) Applicant: Sartorius Stedim Biotech GmbH, Goettingen (DE)

(72) Inventors: Stefan Weisshaar, Goettingen (DE); Mario Deuse, Goettingen (DE); Martin Leuthold, Goettingen (DE); Thomas Krumbein, Goettingen (DE)

(73) Assignee: SARTORIUS STEDIM BIOTECH GMBH (DE)

( * ) Notice: Subject to any disclaimer, the term of this patent is extended or adjusted under 35 U.S.C. 154(b) by 930 days.

(21) Appl. No.: 17/055,987

(22) PCT Filed: Nov. 12, 2019

(86) PCT No.: PCT/EP2019/080988
§ 371 (c)(1),
(2) Date: Nov. 16, 2020

(87) PCT Pub. No.: WO2020/099382
PCT Pub. Date: May 22, 2020

(65) Prior Publication Data
US 2021/0252517 A1 Aug. 19, 2021

(30) Foreign Application Priority Data
Nov. 12, 2018 (DE) ............... 10 2018 128 261.3

(51) Int. Cl.
*B01L 3/00* (2006.01)
*B01F 23/00* (2022.01)
(Continued)

(52) U.S. Cl.
CPC ............. *B01L 9/02* (2013.01); *B01L 3/561* (2013.01); *B01L 9/50* (2013.01); *C12M 23/28* (2013.01);
(Continued)

(58) Field of Classification Search
CPC .... B01L 9/02; B01L 3/561; B01L 9/50; B01L 2300/021; B01L 2300/027; B01L 2300/123; C12M 23/28; C12M 23/48; C12M 23/52
See application file for complete search history.

(56) References Cited

U.S. PATENT DOCUMENTS

| 4,645,171 A | 2/1987 | Heide |
| 8,584,602 B2 | 11/2013 | Isgro |

(Continued)

FOREIGN PATENT DOCUMENTS

| CH | 705298 A1 | 1/2013 | |
| CN | 104470805 A * | 3/2015 | ............. B65B 13/02 |

(Continued)

OTHER PUBLICATIONS

FlexAct "Operating Manual_sartorius stedim_biotech_FlexAct® Central Operating Module (COM)" https://manualzz.com/doc/en/4591030/flexact%C2%AE-central-operating-module--com- (Year: 2011).*

(Continued)

*Primary Examiner* — Jennifer Wecker
*Assistant Examiner* — Oyeleye Alexander Alabi
(74) *Attorney, Agent, or Firm* — Dilworth IP, LLC (57) ABSTRACT

A configurable device arrangement for performing at least one unit operation in a biopharmaceutical process includes a base rack and a plurality of holders for releasable direct or indirect attachment of process components, in particular single-use process components, for the unit operation. The (Continued)

holders are in turn adapted to be releasably attached directly or indirectly to the base rack. The device arrangement further includes a positioning system which defines specific positions for the holders relative to the base rack.

34 Claims, 8 Drawing Sheets (51) Int. Cl.
| | |
|---|---|
| B01F 23/41 | (2022.01) |
| B01F 101/23 | (2022.01) |
| B01L 9/00 | (2006.01) |
| B01L 9/02 | (2006.01) |
| B23Q 17/24 | (2006.01) |
| C07K 14/705 | (2006.01) |
| C12M 1/00 | (2006.01) |
| C12M 1/34 | (2006.01) |
| C12M 3/00 | (2006.01) |
| C12Q 1/04 | (2006.01) |
| C12Q 1/18 | (2006.01) |
| C12Q 1/686 | (2018.01) |
| G01N 21/3577 | (2014.01) |
| G01N 21/359 | (2014.01) |
| G01N 21/39 | (2006.01) |
| G01N 21/45 | (2006.01) |
| G01N 21/64 | (2006.01) |
| G01N 21/77 | (2006.01) |
| G01N 21/78 | (2006.01) |
| G01N 27/414 | (2006.01) |
| G01N 30/12 | (2006.01) |
| G01N 30/68 | (2006.01) |
| G01N 30/70 | (2006.01) |
| G01N 30/72 | (2006.01) |
| G01N 30/88 | (2006.01) |
| G01N 33/00 | (2006.01) |
| G01N 33/18 | (2006.01) |
| G01N 33/50 | (2006.01) |
| G01N 33/53 | (2006.01) |
| G01N 33/543 | (2006.01) |
| G01N 33/68 | (2006.01) |
| G01N 33/74 | (2006.01) |
| G01N 35/00 | (2006.01) |
| G01N 35/10 | (2006.01) |
| G06T 7/00 | (2017.01) |
| G06T 7/90 | (2017.01) |
| H10K 10/46 | (2023.01) |
| H10K 85/00 | (2023.01) |
| H10K 85/20 | (2023.01) |

(52) U.S. Cl.
CPC ............ *C12M 23/48* (2013.01); *C12M 23/52* (2013.01); B01L 2300/021 (2013.01); B01L 2300/027 (2013.01); B01L 2300/123 (2013.01)

(56) References Cited

U.S. PATENT DOCUMENTS

| | | |
|---|---|---|
| 9,167,915 B1 | 10/2015 | Lau |
| 9,622,941 B2 | 4/2017 | Sharpe et al. |
| 9,907,727 B2 | 3/2018 | Sharpe et al. |
| 2008/0149547 A1 | 6/2008 | Schloderer |
| 2010/0294896 A1 | 11/2010 | Sayilgan |
| 2011/0143947 A1* | 6/2011 | Chamberlin ..... G01N 33/56983 506/7 |
| 2013/0019782 A1 | 1/2013 | Isgro |
| 2014/0317951 A1* | 10/2014 | Kauling ................... C07K 1/34 210/450 |
| 2016/0096179 A1* | 4/2016 | Johnson .................... B01L 9/06 422/562 |
| 2019/0144811 A1* | 5/2019 | Heese ..................... C12M 23/28 435/289.1 |
| 2019/0322970 A1* | 10/2019 | Gebauer ................ C12M 23/26 |
| 2020/0347335 A1 | 11/2020 | Schlack |
| 2021/0322994 A1* | 10/2021 | Müller ............. G01N 35/00732 |

FOREIGN PATENT DOCUMENTS

| | | | |
|---|---|---|---|
| DE | 836401 C | 4/1952 | |
| DE | 3616449 A1 | 11/1986 | |
| DE | 102005008620 B3 | 9/2006 | |
| DE | 102009017977 A1 | 10/2010 | |
| DE | 102012222827 A1 * | 6/2014 | ............... B01L 9/50 |
| DE | 102016008655 A1 | 1/2018 | |
| DE | 102017130093 A1 | 6/2019 | |
| WO | WO-2012062580 A1 * | 5/2012 | ........... A47L 9/0036 |

OTHER PUBLICATIONS

Technische Dokumentation. "Operating Manual | Betriebshandbuch FlexAct Central Operating Manual (COM)", Gottingen, Germany, Dec. 31, 2011, 80 pages.

International Search Report issued in International Application No. PCT/EP2019/080988, Issued Dec. 19, 2019, 2 pages.

Technical documentation: "Operating Manual / Betriebshandbuch FlexAct Central Operating Manual (COM)", Dec. 31, 2011, XP 055652560, Göttingen, Germany.

\* cited by examiner

CONFIGURABLE DEVICE ARRANGEMENT FOR PERFORMING AT LEAST ONE UNIT OPERATION IN A BIOPHARMACEUTICAL PROCESS

The invention relates to a configurable device arrangement for performing at least one unit operation in a biopharmaceutical process.

For performing specific unit operations in biopharmaceutical processes in which single-use process components are used, prefabricated standardized device arrangements are often used which can be configured in various ways. An example of such a solution is the FlexAct® system from Sartorius Stedim Biotech GmbH, which is flexibly adaptable and can be used for buffer production, depth filtration, virus inactivation, media preparation, virus removal or integrity testing, among other things. The core of this device arrangement is a compact central multifunction operating module ("central operating module") having a base rack in the form of a stainless steel trolley, various interfaces, a control means and an operating panel. With the FlexAct® system, specific unit operations with selected single-use process components (also known as "single-use assemblies" or "wet-ware", such as bags, hose lines, connectors, filter capsules, etc.) can be performed at least partially in an automated manner.

The device arrangements known from the prior art are subject to specific restrictions. Usually, a device arrangement is designed for a specific process step with a specific volume. A correct installation or conversion of the device arrangement on the user's side is usually only feasible with high effort, which leads to an increased susceptibility to errors. In this context, in particular the fast and correct connection of the single-use process components is a challenge, since the required hose connections reach a high degree of complexity. Individual mounting processes often have to be carried out in pairs. The assembly problem should not be underestimated, since an incorrect mounting can not only lead to a process interruption, but can also result in very high costs, in particular if the medium is lost.

The object of the invention is to simplify the assembly of a device arrangement for performing at least one unit operation in a biopharmaceutical process and to make it more user-friendly.

This object is achieved by a configurable device arrangement having the features of claim 1. Advantageous and useful configurations of the device arrangement according to the invention are specified in the subclaims.

The configurable device arrangement according to the invention for performing at least one unit operation in a biopharmaceutical process comprises a base rack, a plurality of holders for the releasable direct or indirect attachment of process components, in particular single-use process components, for the unit operation, wherein the holders are in turn adapted to be releasably attached directly or indirectly to the base rack, and a positioning system which defines specific positions for the holders relative to the base rack.

Releasable attachment is understood to be a fastening in which the holders or process components can be removed again after attachment without destruction or damage and without great effort.

As will be explained later, the holders provided according to the invention can be either universal holders for different process components or specific holders adapted to a specific type of process component or functional element. A functional element, in turn, can be a specific holder for a process component (filter capsule, hose line, etc.).

The invention is based on the findings that the assembly of a device arrangement based on an existing base rack to which a plurality of process components are to be attached, which are intended for single use only, can be significantly simplified if the process components can be attached at clearly defined positions by means of suitable holders without great mounting effort. The susceptibility to errors during assembling and the expenditure of time required for assembling are thus considerably reduced. Ideally, the complete assembling can be carried out by one person alone without assistance. The device arrangement according to the invention also offers logistical advantages, since uniform components (holders, mounting plates etc.) can be used.

The base rack of the device arrangement according to the invention has a plurality of fastening sites, in particular rails, having position marks. The position marks, e.g. in the form of a scale, permit to define exact positional information for the process components or the holders thereof or for other functional elements. For example, instructions of the type "Mount the holder X for the filter capsule Y on the upper rail of the base rack at position Z" can be specified.

A particular optional aid for the configuration of the device arrangement according to the invention are mounting plates, which are each adapted to be releasably attached to a fastening site of the base rack and/or to an adjacent mounting plate. The mounting plates open up an extended scope for the attachment of the process components. On the one hand, an enlarged mounting surface is provided, and on the other hand, a multitude of defined fastening sites can be specified by the mounting plates.

According to an advantageous embodiment, the mounting plates altogether have a multitude of receptacles, in particular in the form of openings, or holding means for attaching holders or for directly receiving process components. The receptacles or holding means as a whole can be arranged in a grid so that clear coordinates can be specified for the receptacles or holding means (e.g. position [5; 3]=fifth receptacle from the left in the third row from the bottom). However, the mounting plates can also be designed for a specific process setup and prefabricated accordingly such that the receptacles or holding means are provided at specific predetermined sites.

According to a preferred embodiment, the holders have a fastening portion, in particular in the form of a clamp, by means of which the holders are adapted to be releasably attached to the base rack or the mounting plates, in particular by means of a releasable latching or snap-on connection. This enables quick and easy mounting without tools.

As already indicated, the holders provided according to the invention may be configured to hold a specific process component or a specific type of process component. An example of such a holder is a hose fixing element having a plurality of hose receptacles for a local fixing of one or more hose lines. With such a hose fixing element it is possible to permanently maintain defined courses of the hose lines and thus avoid a confusing tangle of hose lines. In addition, such a hose fixing element ensures that undesired loads on the hose lines caused by accidental (indirect) pulling on the hose lines are prevented (strain relief).

To ensure simple but reliable fixing of the hose lines, the diameters of the hose receptacles should be slightly smaller than the diameter of the hose lines to be fixed, so that a clamp connection is achieved. The hose receptacles can in particular be adapted to the standardized hose diameters.

An elastic design of the hose receptacles or of the entire hose fixing element is helpful for receiving the hose lines in the hose fixing element.

According to a particular aspect, the hose receptacles are arranged circumferentially with respect to an axis of the hose fixing element. On the one hand, the circumferential arrangement allows a hose line to be redirected at a specific angle by fixing the hose line in hose receptacles which are not opposite each other. On the other hand, due to the multitude of hose receptacles, it is possible to guide a plurality of hose lines past each other without them interfering with each other.

With a particular configuration of the hose fixing element, it is even possible to fix a plurality of hose lines in the same hose receptacle. The depth of the hose receptacle is accordingly dimensioned such that a plurality of hose lines can be placed one above the other.

According to a further aspect, two or more hose lines can also be placed in different planes in a different way, namely by means of a hose fixing element, in which at least two hose receptacles are arranged one above the other with respect to an axis of the hose fixing element. In this context, a configuration is advantageous in which hose receptacles of a first group are open in a first axial direction and hose receptacles of a second group are open in a second axial direction different from the first direction. This means that hose lines can be inserted into the hose receptacles from different sides of the hose fixing element.

In order to further relieve the hose lines clamped in the hose receptacles and to prevent the hose lines from kinking, it is possible to insert holding elements into the hose receptacles to increase the hose supporting surface.

The hose fixing element can not only be used to fix hose lines but also to hold a functional element. For this purpose, the corresponding functional element has a rigid cylindrical portion which is adapted to the hose receptacles or the supporting surfaces of the holding elements. The length of the cylindrical portion is preferably dimensioned such that it can be inserted into two opposite hose receptacles. This ensures a stable support.

A cover for closing the hose receptacles can be attached to the hose fixing element in order to prevent the hose lines or cylindrical portions of functional elements located in the hose receptacles from slipping out.

Particularly advantageous is an embodiment of the device arrangement according to the invention, in which at least one of the holders is configured as a universal holder having a universal receptacle for releasably receiving a uniform fixing portion, and in which a plurality of functional elements each have the same uniform fixing portion. Due to the universal receptacle and the fixing portions of the functional elements adapted thereto, it is possible to attach different functional elements to the device arrangement using the universal holder. This means that the functional elements do not each require an individual holder specially designed therefor. Rather, the various functional elements can all be attached using the same universal holder. This considerably simplifies the assembling and reduces the number of holder types required for the different functional elements, at best to just one.

The concept of the universal holder having the universal receptacle can be extended. In addition to the universal holder, at least one further holder and/or at least one functional element may have such a universal receptacle. This makes it possible to fix another functional element having a uniform fixing portion directly to a functional element without the need for additional aids.

A functional element having a plurality of uniform fixing portions at different sites offers the advantage to be adapted to be attached in different orientations or positions. This can be of great importance in case of space problems or to ensure a given orientation and/or accessibility of the process component held by the functional element.

Regardless of where the universal receptacle is provided, a latching or snap-on connection may be provided between the universal receptacle and the uniform fixing portion in view of a secure attachment, in particular to prevent the fixing portion from slipping out of the universal receptacle.

Particularly advantageous is an embodiment in which the uniform fixing portion of the functional elements can be received in the universal receptacle in at least two different orientations. Therefore, different orientations of the functional element or of the process component held thereby can be easily achieved.

For example, the uniform fixing portion can substantially be configured as a plate in the shape of a regular polygon having an even number of sides, in particular in the shape of a square. A square fixing portion can be inserted in four different orientations (each rotated by) 90°. For polygons having a larger number of sides, the number of possible orientations can be increased accordingly.

According to a further concept, the uniform fixing portion is substantially configured as an elastically compressible pin which can assume various rotational positions in the universal receptacle. In principle, this design allows a free choice of orientation (in one plane), wherein measures have to be taken, if necessary, to stabilize the fixing portion in the desired rotational position.

A concrete example of a functional element which can be attached in different orientations by means of the concept of the universal receptacle and the uniform fixing portion is a hose holder which has such a uniform fixing portion and an (elastic) holding portion for the local fixing of a hose line (in particular by clamping).

A further example of a functional element of the device arrangement according to the invention is a connecting element which has at least two universal receptacles for releasably receiving a respective uniform fixing portion of a functional element. With such a connecting element, two or more functional elements or holders can be fixed relative to each other.

For the easy and quick attachment of filter capsules, the invention provides a capsule holder which has at least one holding portion for receiving filter capsules of a specific size and which is furthermore provided with at least one uniform fixing portion which is adapted to the universal receptacle of the universal holders or of the functional elements.

In principle, any functional element having at least one uniform fixing portion can benefit from the simplified mounting. If not only one fixing portion, but a plurality of fixing portions are provided, it is also possible to securely attach a larger or heavier process component using a functional element due to the better stability thus achieved.

An example thereof is a component holder, in particular a sensor or valve holder, which has at least two uniform fixing portions and at least one receptacle for a component, in particular for a sensor or for a valve, e.g. a hose pinch valve. Due to the fixing portions of the valve holder, the pressing forces acting on a pinch valve can be absorbed. A further example thereof is a holder for a sampling device.

In a particular embodiment, the sensor holder can further have at least two universal receptacles, in which in particular two hose holders having uniform fixing portions can be inserted. Due to the tube holders, which can thus be attached easily, largely load-free hose connections to the sensor are made possible without much effort.

According to a further aspect of the invention, the device arrangement comprises a plurality of process components and rigid pipes, the process components being fixed in a rigid frame which can be attached to the base rack or to the mounting plates. In this case, the rigid frame can be considered as a functional element allowing the attachment of a pre-assembled unit of process components.

The holders and/or the functional elements and/or the mounting plates of the device arrangement according to the invention are preferably sterilized single-use components, in particular made of plastic. The parts can be advantageously manufactured by injection molding or 3D printing.

The holders and/or the functional elements and/or the mounting plates can themselves be provided with positional information, so that the user does not have to look up the correct position in instructions.

A further measure to simplify mounting is to provide the holders and/or the functional elements and/or the mounting plates with positional information, e.g. with individual markings which each match an individual marking on a fastening site of the base rack.

A further solution provides to equip the holders and/or the functional elements and/or the mounting plates with permanent magnets, only specific predetermined areas of the fastening sites of the base rack being ferromagnetic. The user can immediately see from the noticeable attraction where the mounting of a holder etc. is possible and where not.

According to a further development of the invention, the fastening sites and/or the holders and/or the functional elements and/or the mounting plates have an electronic display. The display can be used in particular to signal a fastening site for a specific holder, to confirm the position and/or to visualize current measured values or other process-relevant information.

Before putting the assembled device arrangement into operation, a simple but reliable check of the correctness of the assembly is desirable. Such a check is possible using a positioning system which is configured for an adjustment of the correct positioning of the holders and/or the functional elements and/or the mounting plates and/or the process components by means of an image recorded by a camera. The image can be taken with the camera of a smartphone or a tablet, for example.

According to a further development of the inventive idea, the holders and/or the functional elements and/or the mounting plates and/or the process components can be connected by radio to a central control means of the device arrangement. By means of the radio link, it is basically not only possible to identify the installed process components, but also to locate them with sufficient accuracy to confirm their correct position in the process assembly.

The holders and/or the functional elements and/or the mounting plates and/or the process components may in particular be provided with RFID tags, the use of which has already proven itself in other technical fields.

Further features and advantages of the invention will become apparent from the description below and from the accompanying drawings to which reference is made and in which.

Figure 1:
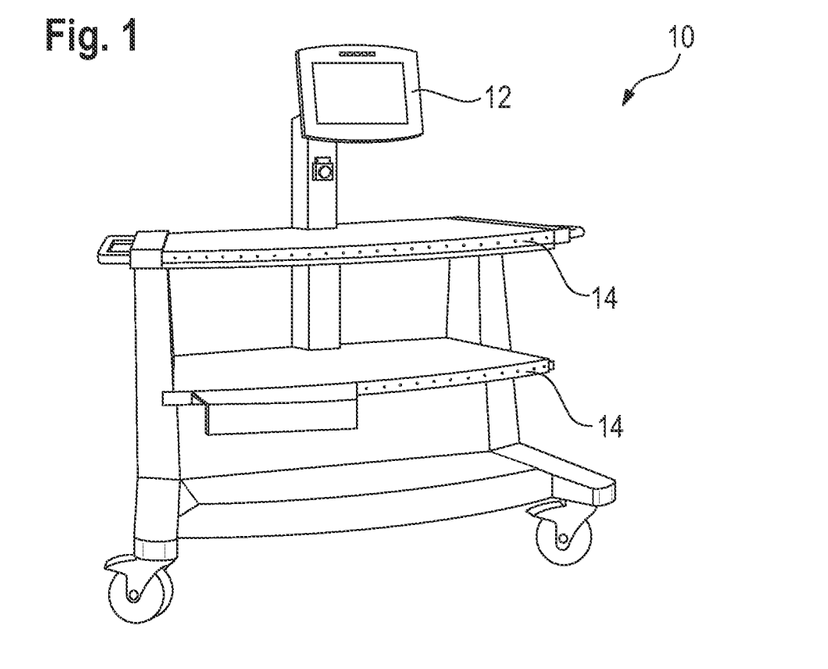
FIG. 1 shows a base rack of a device arrangement according to the invention for performing a unit operation in a biopharmaceutical process.

FIG. 1 shows a base rack 10 of a device arrangement which can be configured in various ways for performing specific unit operations in biopharmaceutical processes using single-use process components. The base rack 10 provided for multiple use is shown here as a stainless steel trolley having numerous interfaces and a display 12.

Figure 2:
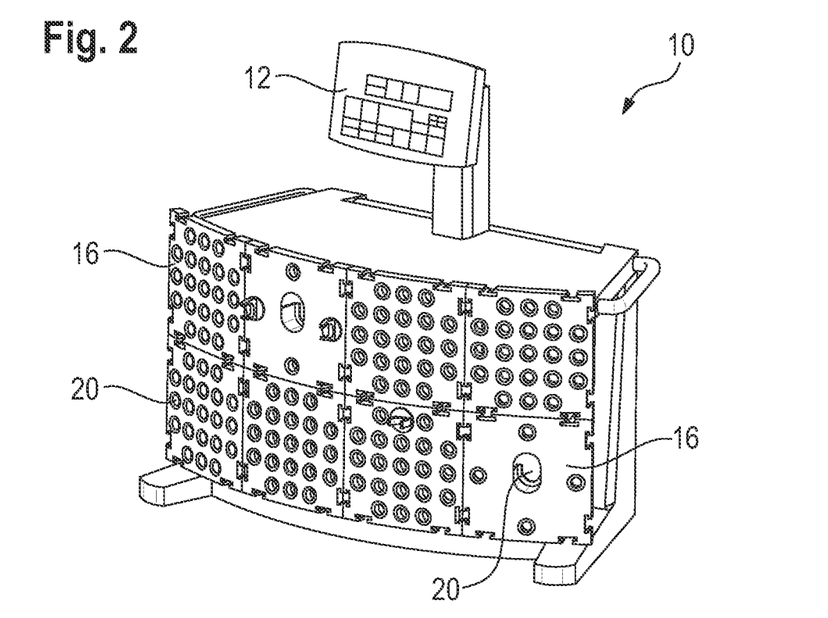
FIG. 2 shows the base rack from FIG. 1 with mounting plates attached thereto.
Figure 3:
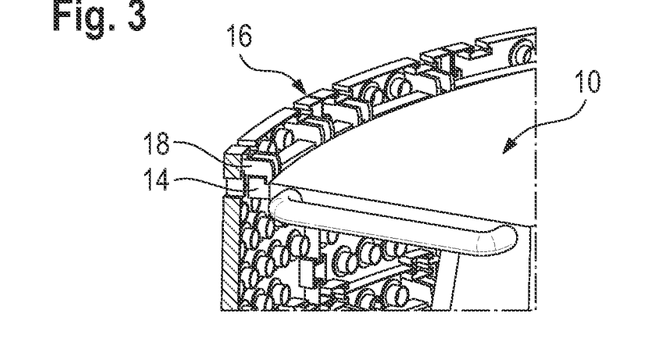
FIG. 3 shows a rear detail view of the mounting plates attached to the base rack.

The base rack 10 has a plurality of rails 14 with markings. As shown in FIGS. 2 and 3, a plurality of mounting plates 16 can be releasably attached to the rails 14. For this purpose, the mounting plates 16 are provided with fastening portions 18, here in the form of clamps, by means of which the mounting plates 16 can be attached firmly, but preferably releasably, to one or more rails 14 of the base rack 10, for example by means of a releasable latching or snap-on connection. In principle, the mounting plates 16 can be attached not only to rails 14 but also to other fastening sites of the base rack 10.

In the example configuration shown in FIGS. 2 and 3, different mounting plates 16 are joined together to form a large, continuous mounting surface. Adjacent mounting plates 16 are connected to each other, preferably in a releasable manner, to generally provide a stable mounting surface.

The mounting plates 16 altogether contain a multitude of receptacles 20, in particular in the form of openings, which are arranged in a grid or are provided at specific predetermined sites. The receptacles 20 are used to attach universal holders (which will be explained in more detail later) or specific holders adapted to specific single-use process components, or they are designed for the direct reception of specific single-use process components. However, in the case of through holes, it is also possible to pass hose lines or other lines or components to the other side of the mounting plates 16.

In addition to or in place of the receptacles 20, the mounting plates 16 may also have other holding means to fix specific components required for the respective process.

Figure 4:
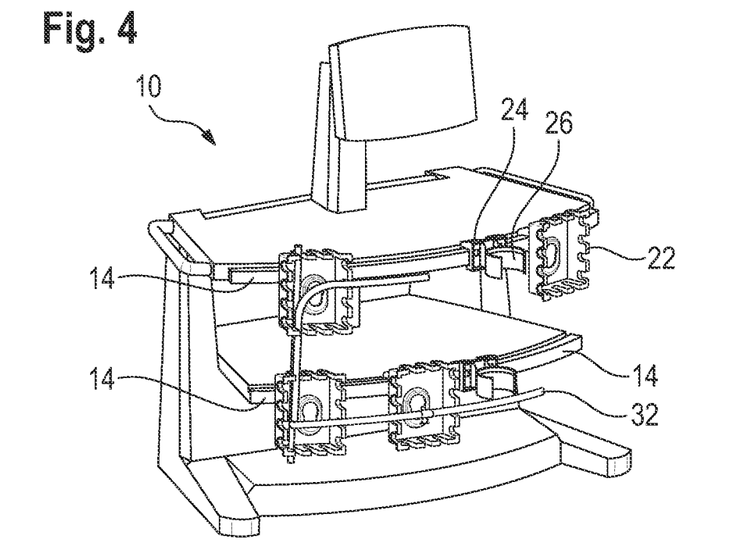
FIG. 4 shows the base rack from FIG. 1 with hose fixing elements and capsule holders attached thereto.

FIG. 4 shows a base rack 10 of the device arrangement in which, by way of example, four hose fixing elements 22 and two universal holders 24 are releasably attached directly, i.e. without mounting plates 16, to the rails 14. One capsule holder 26 is inserted in each of the universal holders 24.

Different holders and functional elements of the device arrangement will be described in detail in the following.

Figure 5:
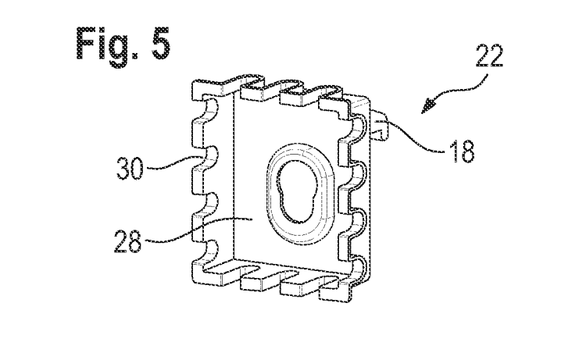
FIG. 5 shows an individual hose fixing element.

FIG. 5 shows a single hose fixing element 22 according to a first variant. A multitude of hose receptacles 30 for the local fixing of one or more hose lines 32 extends from the front side of a square base plate 28 which is substantially square here, and over the entire circumference. The diameters of the hose receptacles 30 are slightly smaller than the diameter of the hose lines 32 to be fixed. The hose receptacles 30 or the entire hose fixing element 22 may be elastic, in particular to facilitate the reception (and, if necessary, the later removal) of relatively stiff hose lines 32 or rigid pipes.

The rear side of the hose fixing element 22 is provided with a fastening portion 18, here in the form of a clamp, by means of which the hose fixing element 22 can be attached firmly, but preferably releasably, to one of the rails 14 of the base rack 10, for example by a releasable latching or snap-on connection. In principle, it is also possible to attach the hose fixing element 22 to another fastening site of the base rack 10 or to a mounting plate 16.

A receptacle which serves to fix a sensor or another component required for the desired process is formed in the base plate 28 of the hose fixing element 22.

As can be seen in FIG. 4, one or more hose lines 32 can be fixed locally by means of a hose fixing element 22, wherein depending on the depth of the hose receptacles 30, one or more hose lines 32 may be fixed per hose receptacle 30.

Usually, it is provided that a hose line 32 is respectively received in two different hose receptacles 30 of a hose fixing element 22. In the simplest case, the hose line 32 is received in two opposite hose receptacles 30 of the hose fixing element 22, so that the hose fixing element 22 supports a straight course of the hose line 32.

However, due to the circumferential arrangement of the hose receptacles 30, it is also possible to redirect hose lines 32 at different angles, e.g. to achieve a stable change of direction by 90° without the risk of kinking the hose line 32. In general, the fixing of the hose lines 32 in the hose receptacles 30 of the hose fixing elements 22 provides for a strain relief of the hose lines 32.

Due to the multitude of hose receptacles 30 in a hose fixing element 22, a plurality of hose lines 32 can be moved past each other in a defined manner without the hose lines 32 affecting each other. Unintentional deflection of a hose line 32, which could then possibly drag along another hose line 32, is prevented by the hose fixing elements 22.

If a sensor or another process component is fixed in the central receptacle of the hose fixing element 22, the hose line 32 leading to or away from this component can be fixed in the hose receptacles 30 such that the hose line connections are not under mechanical tension or only under low mechanical tension.

Figure 6:
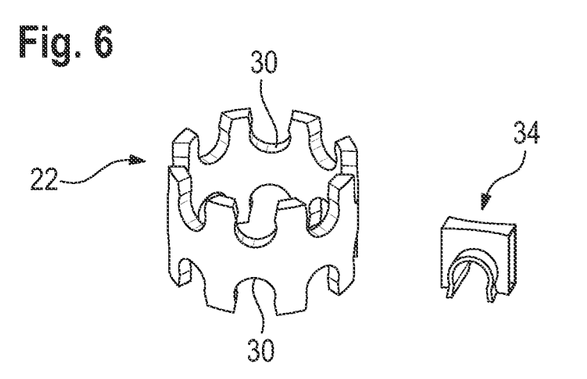
FIG. 6 shows a variant of the hose fixing element with an associated holding element.

FIG. 6 shows another variant of a hose fixing element 22 with an associated holding element 34. The hose fixing element 22 is here configured like a double-sided crown. Based on a ring shape, a plurality of hose receptacles 30 are here also formed over the entire circumference. The hose receptacles 30 of a first group are open in a first axial direction with respect to the center axis of the ring shape, while the hose receptacles 30 of a second group are open in an opposite second axial direction. The hose receptacles 30 of the first and the second group can be arranged directly opposite each other or offset from each other.

Figure 7:
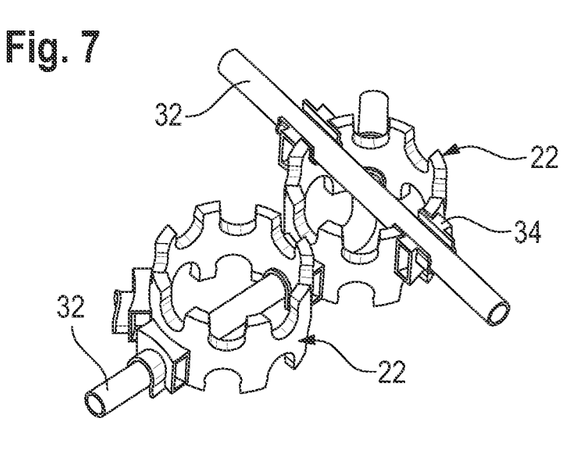
FIG. 7 shows an example configuration including two hose fixing elements.

Due to the double-sided design of this variant of the hose fixing element 22, the hose lines 32 can be guided in two different planes, as shown in FIG. 7. In principle, it is also possible to transfer a hose line 32 from one plane to the other plane.

To reduce the load on the hose lines 32 in the hose receptacles 30 of the hose fixing element 22, holding elements 34 having enlarged hose supporting surfaces may be inserted into the hose receptacles 30. This also applies to the first variant shown in FIGS. 4 and 5 and to further variants of the hose fixing element 22.

Figure 8:
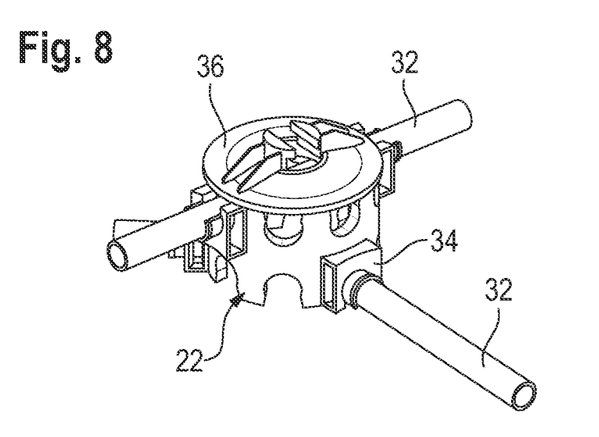
FIG. 8 shows an example configuration including a hose fixing element and a cover.

A further optional functional element for use with a hose fixing element 22 is the cover 36 shown in FIG. 8 as an example. The cover 36 is adapted to the basic shape of the hose fixing element 22 and can be placed so as to close the hose receptacles 30. To this end, the cover 36 can be fixed to the areas between the hose receptacles 30, for example by means of a clamp connection.

Figure 9:
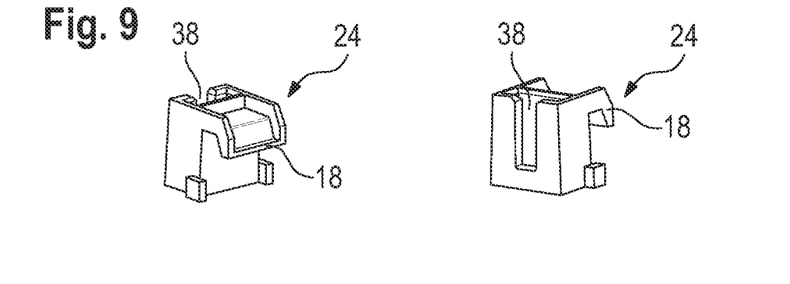
FIG. 9 shows two views of a universal holder.

FIG. 9 shows a universal holder 24 which has a fastening portion 18 on its rear side, here in the form of a clamp, for a firm, preferably releasable attachment to a rail 14, to another fastening site of the base rack 10 or to a mounting plate 16.

On its front side, the universal holder 24 has a universal receptacle 38, which is open at the top and closed at the bottom. The front side of the universal receptacle 38 has a slot-like opening. A standardized fixing portion 40 of a holder, of a guide element or of another functional element can be inserted into the universal receptacle 38 from the top and, if necessary, be removed in the reverse direction. As an option, a releasable latching or snap-on connection can be provided between the universal receptacle 38 and the uniform fixing portion 40.

Figure 10:
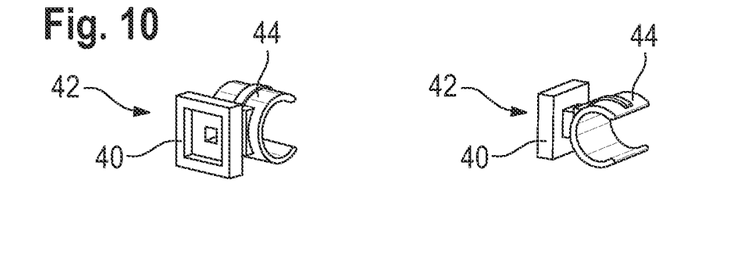
FIG. 10 shows two views of a hose holder.

FIG. 10 shows a hose holder 42, which is intended to be received in a universal holder 24. The hose holder 42 has a uniform fixing portion 40 which is adapted to the universal receptacle 38, which is shown here in the form of a substantially square plate, and from which a transition portion having an integrally molded holding portion 44 extends. The transition portion is dimensioned so as to fit through the slot-like opening of the universal holder 24. A hose line 32 can be clamped into the holding portion 44 of the hose holder 42 and can thus be fixed.

Figure 11:
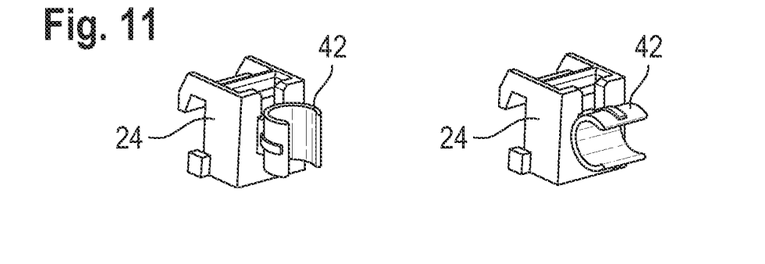
FIG. 11 shows two universal holders with differently inserted hose holders.

As shown in FIG. 11, the hose holder 42 can be inserted in different orientations into the universal receptacle 38 of the universal holder 24 so that a hose line 32 can be fixed in correspondingly different orientations.

Figure 12:
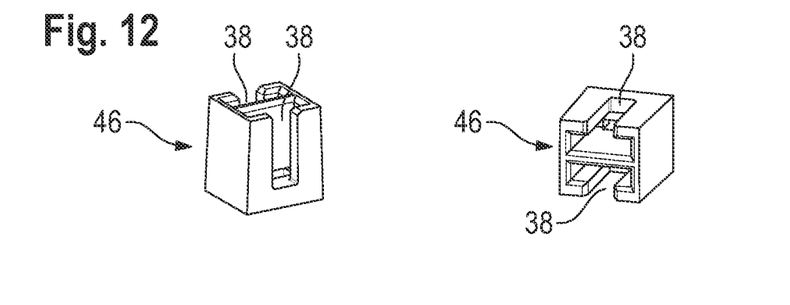
FIG. 12 shows two views of a connecting element.
Figure 13:
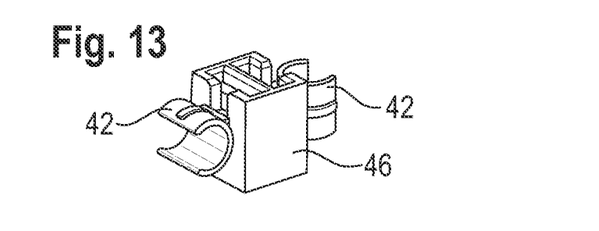
FIG. 13 shows a connecting element with two differently inserted hose holders.

FIG. 12 shows a connecting element 46 having two opposite universal receptacles 38. The universal receptacles 38 are configured in the same way as the universal holders 24 described above. If two hose holders 42 are inserted into the connecting element 46 as shown in the example configuration of FIG. 13, it is possible to fix two hose lines 32 in specified orientations relative to each other.

The connecting element 46 may also have more than two universal receptacles 38, and other functional elements having uniform fixing portions 40 may be used instead of the hose holders 42.

Figure 14:
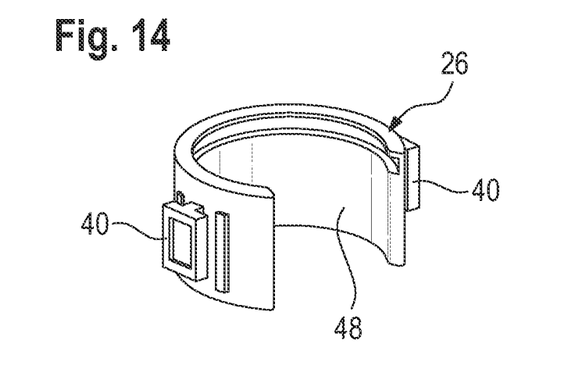
FIG. 14 shows a capsule holder.
Figure 15:
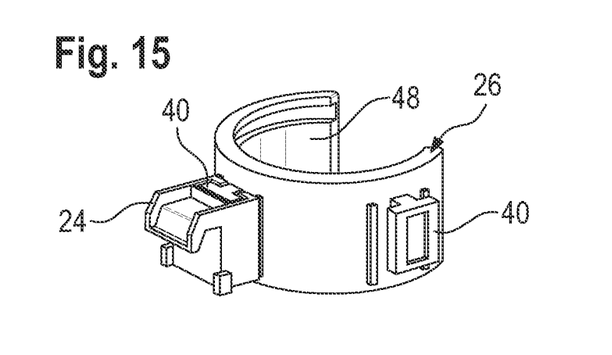
FIG. 15 shows a universal holder with an inserted capsule holder.

FIG. 14 shows a capsule holder 26, which is intended to be received in a universal holder 24, as shown in FIG. 15. The capsule holder 26 is basically similar in design to the hose holder 42 described above. The holding portion 48 of the capsule holder 26 is however provided for receiving filter capsules (filter cartridges) of a specific size (diameter) and is dimensioned accordingly.

Otherwise, as with the hose holder 42, a uniform fixing portion 40, here again in the form of a substantially square plate, and a narrow transition portion between the fixing portion 40 and the holding portion 48 are provided. The universal receptacle 38 of the universal holder 24 and the uniform fixing portion 40 of the capsule holder 26 are again adapted to each other such that the capsule holder 26 can be inserted into the universal holder 24 in different orientations. This makes it possible to fix a filter capsule vertically, horizontally or, if necessary, in another orientation.

A plurality of uniform fixing portions 40 are integrally formed over the (not completely closed) holding portion 48 of the capsule holder 26. The direction from which a filter capsule can be pressed into the capsule holder 26 depends on which of the uniform fixing portions 40 is inserted into the universal receptacle 38 of the universal holder 24.

Figure 16:
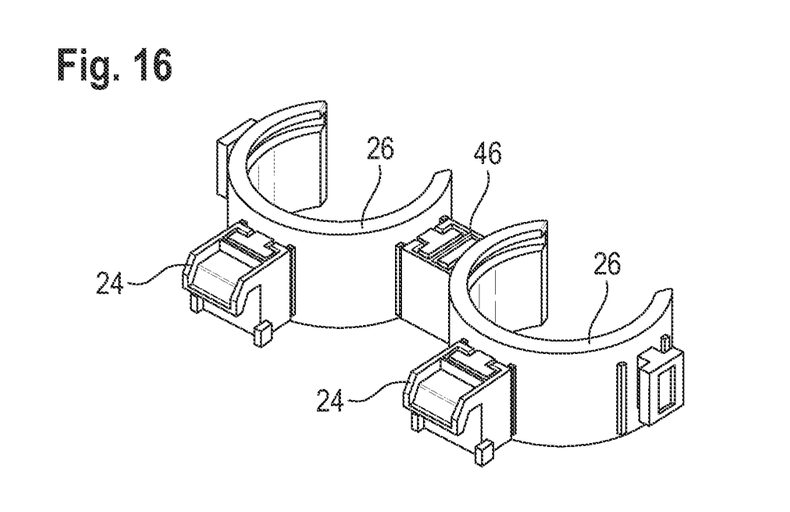
FIG. 16 shows an example configuration including two universal holders, two capsule holders and one connecting element.

FIG. 16 shows an example configuration in which two capsule holders 26 are connected to each other by means of a connecting element 46 and are each inserted into a universal holder 24. Such an assembly can be attached as a stable unit to the base rack 10 of the device arrangement or to a mounting plate 16. The use of such connecting elements 46 reduces the number of individual components and reduces the assembly complexity for the user. The use of standardized connecting elements 46 which are identical in design can also minimize the number of connection steps required, which reduces the risk of leakage and contamination.

Figure 17:
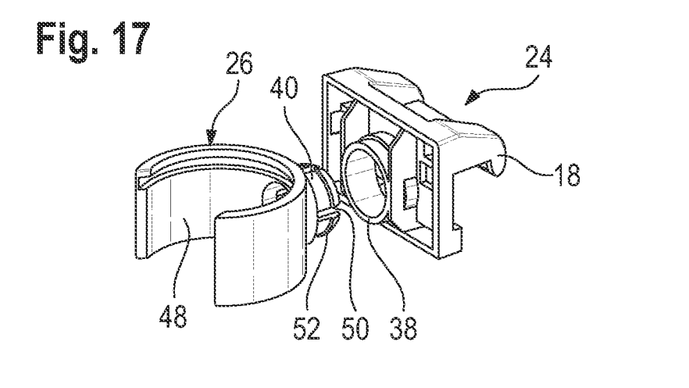
FIG. 17 shows a variant of the universal holder and a variant of the capsule holder.
Figure 18:
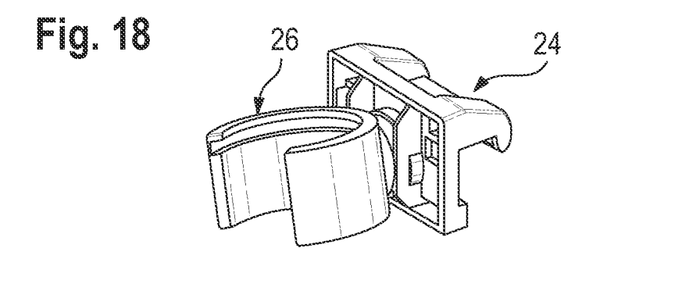
FIG. 18 shows the universal holder and the capsule holder from FIG. 17 in the mounted state.

FIG. 17 shows other variants of the universal holder 24 and of the capsule holder 26 which are adapted to each other. Here, the universal holder 24 has a circular universal receptacle 38 into which a uniform fixing portion 40, here in the form of an elastically compressible pin, of the capsule holder 26 or of another functional element can be clipped. To this end, the uniform pin has recesses 50 distributed around the circumference so that the portions located therebetween can be pressed inwards. At its free end, the uniform pin has latching portions 52 which, due to the elasticity of the uniform pin, can engage behind the rear edge of the round universal receptacle 38. The special feature of this type of connection is that the capsule holder 26 (or any other functional element having such a uniform pin) can assume various rotational positions in the universal receptacle 38, as indicated in FIG. 18.

Figure 19:
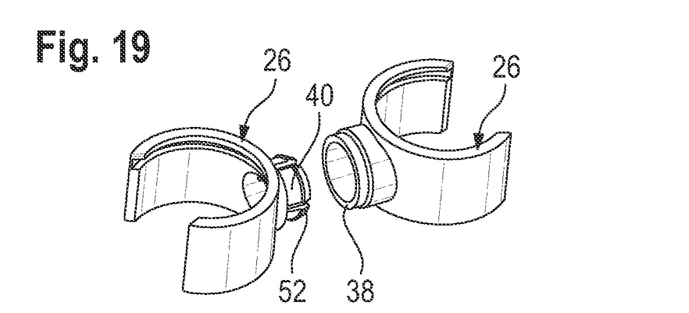
FIG. 19 shows two variants of the capsule holder.
Figure 20:
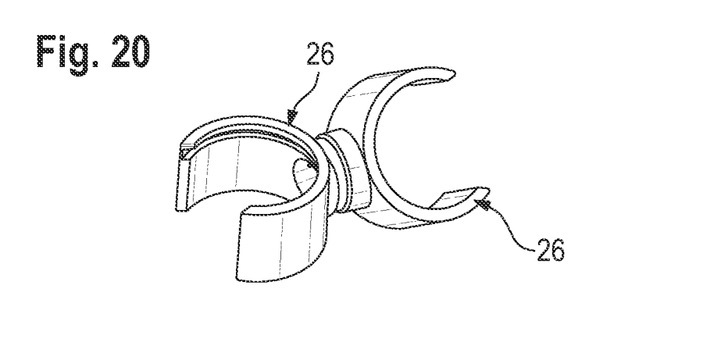
FIG. 20 shows the capsule holder from FIG. 19 in the mounted state.

FIG. 19 shows two capsule holders 26 which can be connected to each other. One of these two capsule holders 26 corresponds to the capsule holder 26 shown in FIGS. 17 and 18 with an elastic uniform pin as fixing portion 40. The other capsule holder 26 has a universal receptacle 38 on the outside of its holding portion 48 which is designed in the same way as that of the universal holder 24 shown in FIGS. 17 and 18. The two capsule holders 26 can be connected to each other by clipping the uniform pin of one capsule holder 26 into the universal receptacle 38 of the other capsule holder 26, as already described above. In the mounted state, the capsule holders 26 can be rotated relative to each other, as indicated in FIG. 20, i.e. the filter capsules received therein can be arranged in a desired orientation relative to each other.

Figure 21:
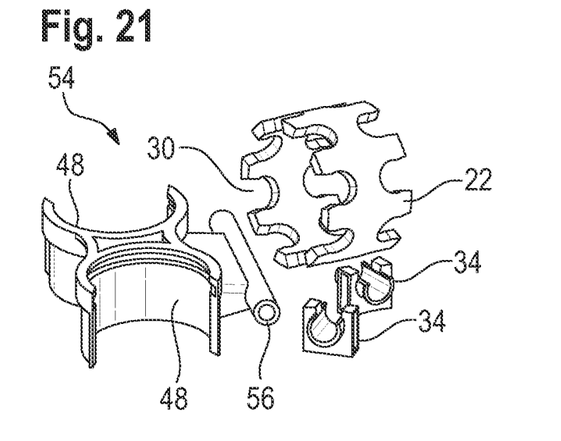
FIG. 21 shows a hose fixing element, a double capsule holder and two holding elements.

FIG. 21 shows an exemplary kit including a hose fixing element 22, two holding elements 34 and a double capsule holder 54. The hose fixing element 22 and the holding elements 34 have already been described with reference to FIGS. 6 to 8, so that it is not necessary to explain them further. The double capsule holder 54 has two holding portions 48 which are firmly connected to each other and into which one respective filter capsule can be inserted. A connecting portion which is adjoined by a cylindrical portion 56 extends from the two holding portions 48. The cylindrical portion 56 is adapted to the supporting surfaces of the holding elements 34.

Figure 22:
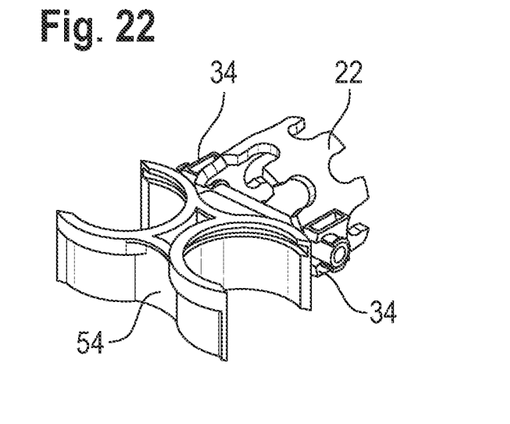
FIG. 22 shows the components from FIG. 21 in the mounted state.

As shown in FIG. 22, the two holding elements 34 can be inserted into opposite hose receptacles 30 of the hose fixing element 22 to receive the cylindrical portion 56 of the double capsule holder 54. In this context, it is advantageous that the holding elements 34 are configured so as to be elastic. Depending on the orientation in which the hose fixing element 22 is attached to the base rack 10 of the device arrangement or to a mounting plate 16, the orientation of the filter capsules received in the double capsule holder 54 changes accordingly.

Figure 23:
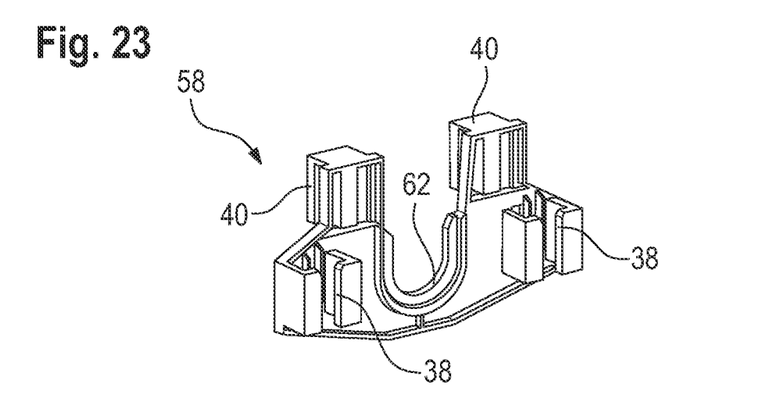
FIG. 23 shows a sensor holder.

FIG. 23 shows a component holder 58 by means of which a sensor 60 (see FIG. 24) or another component can be attached to the base rack 10 of the device arrangement or to a mounting plate 16. The rear side of the component holder 58 has two integrally molded, uniform fixing portions 40 that are adapted to the universal receptacles 38 of the previously described universal holders 24. Two universal receptacles 38 of this kind are formed on the front side of the component holder 58. A receptacle 62 for a sensor 60 or another component that can be inserted therein is formed in the middle.

Figure 24:
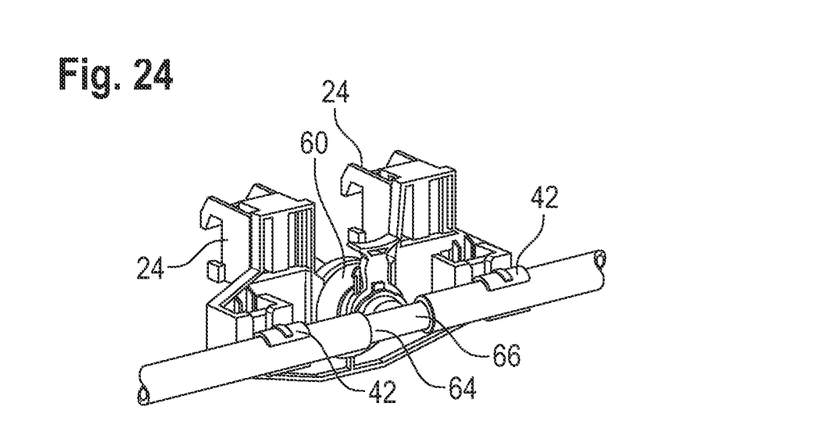
FIG. 24 shows an example configuration including two universal holders, a sensor holder, a sensor, two hose holders and two hose lines.

FIG. 24 shows an example configuration including such a component holder 58. The two uniform fixing portions 40 of the component holder 58 are inserted into the universal receptacles 38 of two universal holders 24, which in turn may be attached to a rail 14 of the base rack 10 of the device arrangement. Two hose holders 42 are inserted into the universal receptacles 38 of the component holder 58. A sensor 60 having two fluid connections 64, 66 is received in the receptacle 62. The components are adapted to each other such that two hose lines 32 can be received in the hose holders 42 and can be connected to the fluid connections 64, 66 of the sensor 60 without significant mechanical stress.

Figure 25:
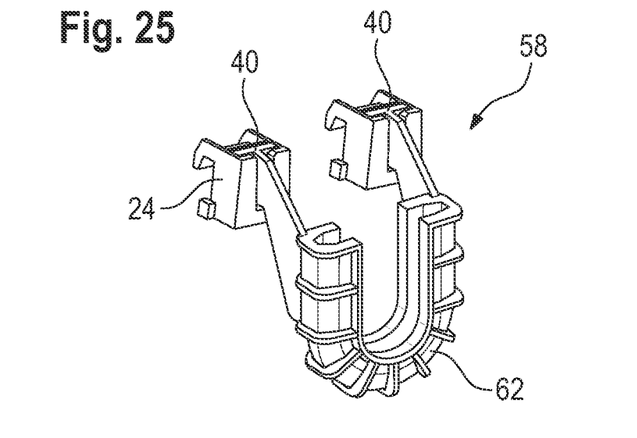
FIG. 25 shows an example configuration including two universal holders and a valve holder.

FIG. 25 shows another variant embodiment of the component holder 58 by means of which a valve, more precisely a hose pinch valve, can be attached to the base rack 10 of the device arrangement or to a mounting plate 16. In this case, the receptacle 62 is adapted to such a valve. The fixing portions 40 of the component holder 58 can absorb the pressing forces acting on the hose pinch valve.

Figure 26:
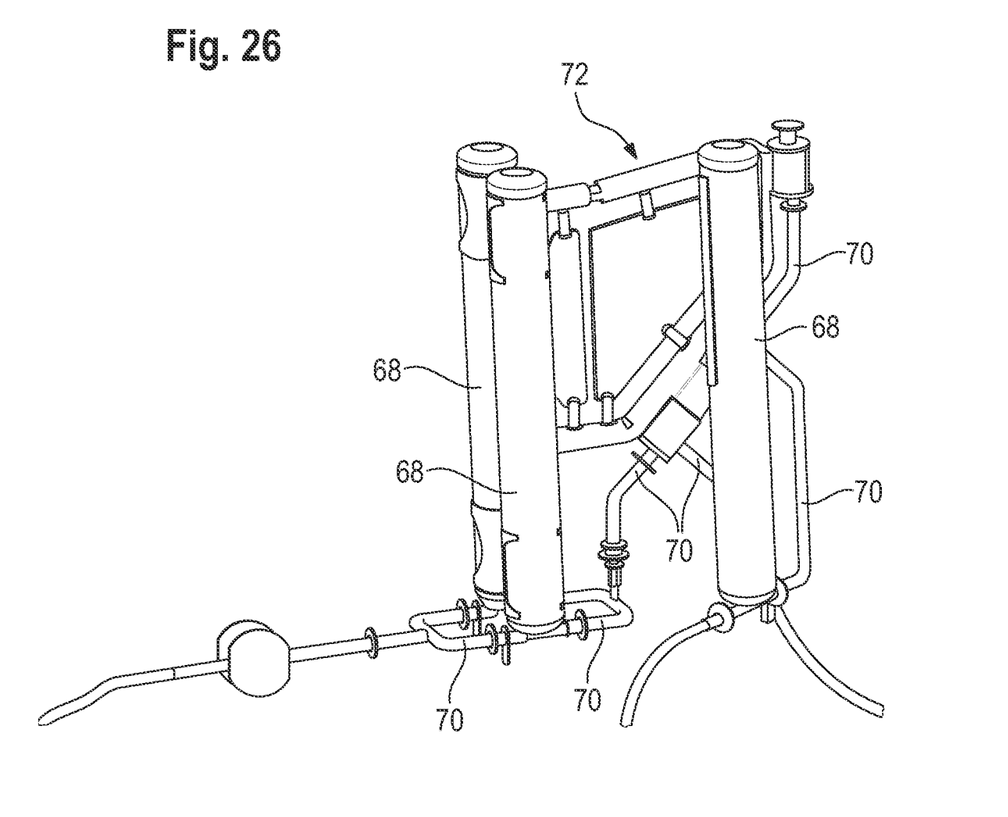
FIG. 26 shows a partial assembly of a process device arrangement including filter capsules, frame elements and rigid pipe connections.

FIG. 26 shows a partial assembly of a process device arrangement with a plurality of filter capsules 68. The filter capsules 68 are at least partially integrated into the process device by rigid pipes 70. In order to ensure a stable arrangement of the filter capsules 68 and other components relative to each other, a rigid frame 72 is provided, which may be composed of a plurality of individual frame elements, if necessary. The filter capsules 68 and other components are fixed in the frame 72 such that they cannot move relative to each other. In this way, loads on the pipes 70 and the connections of the components are avoided. The frame 72 can be attached as a whole to the base rack 10 or to mounting plates 16 of the device arrangement, for example using the universal holders 24 described above. For this purpose, the frame is provided with uniform fixing portions 40.

The holders and functional elements shown in the figures, which are intended for direct or indirect attachment to the base rack 10, are only exemplary designs. Specific functional portions (e.g. universal receptacles 38, fixing portions 40, holding portions 44, 48 etc.) and/or properties (elasticity etc.) of the functional elements can be provided in any combination. The holders and functional elements are preferably made of plastic and can usually be produced by injection molding or 3D printing and sterilized before delivery.

In order to support the simplest and most error-free process setup possible, in particular with regard to the attachment of the single-use process components to the base rack 10 of the device arrangement, one or more of the following measures may be provided, in particular to define clear assembly positions and conditions:

- The rails 14 of the base rack 10 and/or other fastening sites of the base rack 10 and/or the mounting plates 16 (hereinafter generally referred to as fastening sites only) are provided with position marks, e.g. with a punched scale.
- The universal holder 24 or other holders or functional elements, such as the hose fixing elements (hereinafter generally referred to as holders only), which are to be attached to fastening sites, are provided with position markings referring to the position marks.
- A construction plan for the process setup of the device arrangement contains positional information for the holders.
- The holders are provided with individual markings, each of which matches an individual marking on a fastening site.
- The holders are provided with permanent magnets, and only specific predetermined areas of the fastening sites are ferromagnetic, so that the user can see where to place the holders due to magnetic attraction.
- The fastening sites have an electronic display to signal where to place each holder depending on the selected process setup.
- The holders have an electronic display to confirm the position thereof (independent of a control means of the device arrangement). The display of the holders can be used alternatively or additionally to visualize current measured values or other process relevant information.
- An adjustment of the correct positioning of the holders and/or of the process components is carried out by means of a camera (e.g. of a smartphone or a tablet) and an image evaluation.
- The holders and/or the process components attached therewith can be connected by radio to a central control means. The holders and/or the process components can for example be provided with RFID tags which can be read by a reader of the control means. By means of the radio link, it is possible to identify the installed process components and/or confirm the correct position thereof in the process setup. An automatic adoption of process parameters (e.g. operating pressure, type of process) is thus also possible.

LIST OF REFERENCE NUMERALS 10 base rack
12 display
14 rails
16 mounting plates
18 fastening portion
20 receptacles
22 hose fixing element
24 universal holder
26 capsule holder
28 base plate
30 hose receptacles
32 hose lines
34 holding element
36 cover
38 universal receptacle
40 fixing portion
42 hose holder
44 holding portion of the hose holder
46 connecting element
48 holding portion of the capsule holder
50 recesses
52 latching portions
54 double capsule holder
56 cylindrical portion
58 component holder
60 sensor
62 receptacle for component
64 fluid connection
66 fluid connection
68 filter capsules
70 pipes
72 frame

The invention claimed is:

1. A configurable device arrangement for performing at least one unit operation in a biopharmaceutical process, the device arrangement comprising:
   a base rack, including a plurality of fastening rails having position marks,
   a plurality of holders for releasable direct or indirect attachment of process components, being single-use process components, for the unit operation, wherein the holders are in turn adapted to be releasably attached directly or indirectly to the base rack,
   a positioning system which defines specific positions for the holders relative to the base rack, and
   a plurality of mounting plates which are each adapted to be releasably attached by means of latching or snap-on connections to the plurality of fastening rails of the base rack at predetermined positions indicated by the position marks,
   wherein the plurality of mounting plates are joined together by attaching them to adjacent mounting plates in a releasable manner to form a continuous and stable mounting surface, and the plurality of mounting plates altogether have a multitude of receptacles, in a form of openings, or holding means for attaching the holders or for directly receiving the process components, the multitude of receptacles or the holding means as a whole being arranged in a grid or being provided at specific predetermined sites.

2. The device arrangement according to claim 1, characterized in that the holders have a fastening portion, in a form of a clamp, by means of which the holders are adapted to be releasably attached to the base rack or to the mounting plates by means of a releasable latching or snap-on connection.

3. The device arrangement according to claim 1, characterized in that at least one of the holders is configured as a hose fixing element having a plurality of hose receptacles for a local fixing of one or more hose lines.

4. The device arrangement according to claim 3, characterized in that diameters of the hose receptacles are slightly smaller than a diameter of the one or more hose lines to be fixed.

5. The device arrangement according to claim 3, characterized in that the hose receptacles are elastic or an entirety of the hose fixing element is elastic.

6. The device arrangement according to claim 3, characterized in that the hose receptacles are arranged circumferentially with respect to an axis of the hose fixing element.

7. The device arrangement according to claim 3, characterized in that a depth of the hose receptacles is dimensioned such that a plurality of hose lines can be fixed therein.

8. The device arrangement according to claim 3, characterized in that at least two of the plurality of hose receptacles are arranged one above another with respect to an axis of the hose fixing element, wherein a first one of the at least two of the plurality of hose receptacles is open in a first axial direction and a second one of the at least two of the plurality of hose receptacles is open in a second axial direction different from the first direction.

9. The device arrangement according to claim 3, characterized in that holding elements are inserted into the hose receptacles to increase a hose supporting surface.

10. The device arrangement according to claim 3, characterized in that a functional element has a rigid cylindrical portion which is adapted to the hose receptacles or supporting surfaces of holding elements.

11. The device arrangement according to claim 3, further comprising at least one cover for closing at least one hose receptacle.

12. The device arrangement according to claim 1, characterized in that at least one of the holders is configured as a universal holder having a universal receptacle for releasably receiving a uniform fixing portion, and in that a plurality of functional elements each have a same uniform fixing portion.

13. The device arrangement according to claim 12, characterized in that, apart from the universal holder, at least one further holder and/or at least one functional element has a universal receptacle.

14. The device arrangement according to claim 12, characterized in that at least one functional element has a plurality of the same uniform fixing portions.

15. The device arrangement according to claim 12, characterized in that a latching or snap-on connection is provided between the universal receptacle and the uniform fixing portion.

16. The device arrangement according to claim 12, characterized in that the uniform fixing portion of the functional elements can be received in at least two different orientations in the universal receptacle.

17. The device arrangement according to claim 16, characterized in that the uniform fixing portion is substantially configured as a plate in a shape of a regular polygon with an even number of sides.

18. The device arrangement according to claim 16, characterized in that the uniform fixing portion is substantially configured as an elastically compressible pin which can assume different rotational positions in the universal receptacle.

19. The device arrangement according to claim 12, further comprising at least one hose holder having the same uniform fixing portion and a holding portion for a local fixing of one or more hose lines.

20. The device arrangement according to claim 12, further comprising at least one connecting element which has at least two universal receptacles for releasably receiving a respective uniform fixing portion of a functional element.

21. The device arrangement according to claim 12, further comprising at least one capsule holder which has at least one uniform fixing portion and at least one holding portion for receiving filter capsules of a specific size.

22. The device arrangement according to claim 12, further comprising at least one component holder, being a sensor or valve holder, which has at least two uniform fixing portions and at least one component receptacle for a sensor or a valve.

23. The device arrangement according to claim 22, characterized in that the at least one component holder has at least two universal receptacles into which two of the holders having the uniform fixing portion can be inserted.

24. The device arrangement according to claim 1, further comprising a plurality of the process components and rigid pipes, wherein the process components are fixed in a rigid frame which is adapted to be attached to the base rack or to the mounting plates.

25. The device arrangement according to claim 1, characterized in that the holders, functional elements, or the mounting plates are sterilized single-use components made of plastic.

26. The device arrangement according to claim 1, characterized in that the holders, functional elements, or the mounting plates are provided with positional information with individual markings which each match an individual marking on a fastening site of the base rack.

27. The device arrangement according to claim 1, characterized in that the holders, functional elements, or the mounting plates are provided with permanent magnets and only specific predetermined areas of the fastening sites of the base rack are ferromagnetic.

28. The device arrangement according to claim 1, characterized in that the fastening sites, the holders, functional elements, or the mounting plates have an electronic display.

29. The device arrangement according to claim 1, characterized in that the positioning system is configured for an adjustment of a correct positioning of the holders, functional elements, the mounting plates, or the process components by means of an image recorded by a camera.

30. The device arrangement according to claim 1, characterized in that the holders, functional elements, the mounting plates, or the process components can be connected by radio to a central control means of the device arrangement.

31. The device arrangement according to claim 30, characterized in that the holders, functional elements, the mounting plates, or the process components are provided with RFID tags.

32. The device arrangement according to claim 1, wherein the plurality of mounting plates include clamps for releasably attaching the mounting plates to one or more of the fastening rails of the base rack.

33. The device arrangement according to claim 1, wherein adjacent ones of the plurality of mounting plates are joined together in a releasable manner.

34. The device arrangement according to claim 1, wherein the mounting surface formed by the plurality of mounting plates form extends vertically along the base rack, wherein at least a portion of the receptacles extend horizontally through the mounting surface formed by the plurality of mounting plates.

* * * * *